US006906190B2

(12) United States Patent
Yao et al.

(10) Patent No.: US 6,906,190 B2
(45) Date of Patent: Jun. 14, 2005

(54) INHIBITORS FOR DE NOVO-RNA POLYMERASES AND METHODS OF IDENTIFYING TARGETS FOR SAME

(75) Inventors: Nanhua Yao, Irvine, CA (US); Haoyun An, Carlsbad, CA (US); Todd Appleby, Laguna Niguel, CA (US); Shahul Nilar, Irvine, CA (US); Yili Ding, Fountain Valley, CA (US); Zhi Hong, Aliso Viejo, CA (US)

(73) Assignee: Ribapharm Inc., Costa Mesa, CA (US)

( * ) Notice: Subject to any disclaimer, the term of this patent is extended or adjusted under 35 U.S.C. 154(b) by 44 days.

(21) Appl. No.: 10/330,369

(22) Filed: Dec. 27, 2002

(65) Prior Publication Data

US 2003/0187000 A1 Oct. 2, 2003

Related U.S. Application Data

(60) Provisional application No. 60/346,680, filed on Jan. 4, 2002.

(51) Int. Cl.[7] .................. C07D 473/16; C07D 473/18; C07D 473/30; C07D 473/34; A61P 31/14
(52) U.S. Cl. .................. 544/276; 544/265; 544/277; 536/27.6; 536/27.61
(58) Field of Search .................. 544/265, 276, 544/277; 536/27.6, 27.61

(56) References Cited

U.S. PATENT DOCUMENTS

| | | | | |
|---|---|---|---|---|
| 3,498,970 A | * | 3/1970 | Kumashiro et al. | 536/27.61 |
| 3,520,873 A | * | 7/1970 | Dietmann et al. | 536/27.8 |
| 4,774,325 A | * | 9/1988 | Casadio et al. | 536/27.7 |
| 5,086,056 A | * | 2/1992 | Janssens et al. | 544/264 |
| 5,091,432 A | * | 2/1992 | Glasky | 544/276 |
| 5,563,125 A | * | 10/1996 | Sufrin et al. | 536/122 |
| 5,786,359 A | * | 7/1998 | Reitz et al. | 544/276 |
| 6,288,069 B1 | * | 9/2001 | Glasky | 514/263.3 |
| 6,297,226 B1 | * | 10/2001 | Glasky | 544/265 |

OTHER PUBLICATIONS

Marc Pignot, European Journal of Organic Chemistry vol. 2000, Issue 3, pp. 549–555.*
Krzysztof Palczewski, Biochemistry vol. 29, No. 26 pp 6276–6282, 1990.*
Lowrie M. Beacham, Journal of Organic Chemistry vol. 44, No. 18 pp 3100–3101, 1979.*
Hampton, Journal of Medicinal Chemistry vol. 11, No. 6: Nov. 1968 pp 1229.*
Parikh, Journal of the American Chemical Society vol. 79, No. 11: Jun. 5, 1957 pp 2778–2781.*
Maag, Journal of Medicinal Chemistry vol. 35, No. 8: Apr. 17, 1992 pp 1440–1451.*

* cited by examiner

Primary Examiner—Mark L. Berch
(74) Attorney, Agent, or Firm—Brown Raysman Millstein Felder & Steiner LLP

(57) ABSTRACT

A polymerase inhibitor has first moiety coupled to a second moiety via an optional linker in which the first moiety binds to an initiation nucleotide binding site of a polymerase and forms at least two hydrogen bonds with an RNA template strand that is associated with the polymerase, and in which the second moiety comprised a compound that binds to a site proximal to the nucleotide binding site of the polymerase and thereby increases the affinity of the polymerase inhibitor to the polymerase.

2 Claims, 10 Drawing Sheets

INHIBITORS FOR DE NOVO-RNA POLYMERASES AND METHODS OF IDENTIFYING TARGETS FOR SAME

This application claims the benefit of U.S. provisional application with the Ser. No. 60/346,680, which was filed Jan. 4, 2002, and which is incorporated herein by reference.

FIELD OF THE INVENTION

The field of the invention is compositions and methods for inhibition of de novo-RNA polymerases, and particularly of the RNA-dependent-RNA polymerase of the hepatitis C virus.

BACKGROUND OF THE INVENTION

The Hepatitis C virus (HCV) causes one of the worlds most pandemic and insidious diseases. According to the World Health Organization, there are approximately 170 million carriers worldwide with a prevalence up to 0.5–10% (Lancet 351:1415 (1998)), while in the United States, almost four million individuals are afflicted (Alter and Mast, Gastroenterol. Clin. North Am. 23:437–455 (1994)). Unfortunately, 75–85% of people infected will develop a chronic infection, which may ultimately lead to cirrhosis and hepatocellular carcinoma in 10–20% and 1–5%, respectively, of chronically infected people (Cohen, Science 285:26–30 (1999)).

The causative agent, hepatitis C virus, was identified in 1989 and has accounted for 50–60% of the non-A, non-B transfusion associated hepatitis (Alter, et al., N. Engl. J. Med. 321: 1494–1500 (1989); Choo, et al., Science 244:359–362 (1989); Kuo, et al., Science 244:362–364 (1989)). More than 100 strains of the virus have since been identified, and have been grouped into six major genotypes that tend to cluster in different regions of the world (Simmonds, Current Studies in Hematology and Blood Transfusion, Reesink, ed., Karger, Basel, pp. 12–35 (1994); van Doorn, J. Med. Vir. 43:345–356 (1994)).

HCV, a member of the Flaviviridae family, is a positive-sense, single-stranded RNA virus with genome size of approximately 9.6 kb (Heinz, Arch. Virol. Suppl. 4:163–171 (1992); Mizokami and Ohba, Gastroenterol. JPN 28 Suppl5:42–44 (1993); Ohba, et al., FEBS Lett. 378:232–234 (1996); Takamizawa, et al., J. Virol. 65: 1105–1113 (1991). The genomic RNA encodes a polyprotein of approximately 3000 amino acid residues in the order of $NH_2$—C— E1-E2-p7-NS2-NS3-NS4A-NS4B-NS5A-NS5B—COOH (Lohmann, et al., J. Hepatol. 24: 11–19(1996); Simmonds, Clin. Ther. 18 Suppl. B:9–36 (1996). The polyprotein undergoes subsequent proteolysis by host and viral enzymes to yield the mature viral proteins (Grakoui, et al., J. Viral. 67:1385–1395 (1993); Shimotohno, et al., J. Hepatol. 22:87–92 (1995). HCV NS5B is essential for the virus replication and is a viral coded RNA dependent RNA polymerase carrying various functions, including copying the negative strand from the positive strand, and generating multiple copies of positive infectious RNA from the negative template strand.

To date, interferon-alpha and newer versions of longer lasting pegylated interferon monotherapy as well as in combination therapy with ribavirin (Rebetron, Schering-Plough, Kenilworth, N.J.) are among the few approved treatments of hepatitis C. However, typically less than 10% of patients respond to interferon-alpha monotherapy, and 41% of patients respond to combination therapy (Reichard, et al., Lancet 351:83–87 (1998). Therefore, it has become increasingly important to develop more effective antiviral agents against the various viral targets to combat hepatitis C. Among the most promising antiviral targets in chronic HCV infection are the replication enzymes, RNA-binding proteins, viral entry proteins and enzymes required for the virus' maturation processes, and many of those targets have been thoroughly investigated.

For example, the crystal structure of the HCV RNA dependent RNA polymerase has been determined to help design inhibitors for this enzyme. Expectedly, NS5B has been found to share various canonical features of other polymerases. Among other things, NS5B is folded from a single peptide chain into an overall shape of a right hand with three sub-domains: palm, thumb and fingers. The catalytic residues Asp318, Asp319 and Asp220 are located at the palm and encircled by palm, thumb and finger domains, while the thumb and finger domains are interconnected through extended loops. The channel between thumb and fingers define the RNA template-binding site. The NTP is fed through the back channel defined by the three domains and a linkage between thumb and fingers. The duplex RNA is released through a channel on the opposite side of the NTP channel. One particular structural feature in the HCV RNA polymerase is an anti-parallel β-loop that extends from the thumb domain toward the finger domain and is unique among all known polymerases. The cavity between this loop and the active site define the RNA primer-binding site (i.e., initiation nucleotide binding site for HCV). However, despite the relatively extensive knowledge of the molecular architecture of NS5B, design of suitable inhibitors has significantly lagged behind the expectations. For example, targeting of the initiation nucleotide binding site appeared not to be sufficiently promising to many groups for designing of an inhibitor, since the affinity of this site for its natural substrate (the initiation nucleotide) is already relatively low (in the range of $10^{-3}$~$10^{-4}$ M).

Alternatively, chemical modification of enzymes may be a useful tool in designing drugs that interrupt the catalytic activity of enzymes (e.g., suicide inhibitors). Chemical modification of enzymes to alter their specificity and catalytic activity has been studied for many years (Per Berglund, Grace DeSantis, Michele R. Stabile, Xiao Shang, Marvin Gold, Richard R. Bott, Thomas P. Graycar, Tony Hing Lau, Colin Mitchinson, J. Brayan Jones, J. Am. Chem. Soc. 1997, 119,5265–5266; Kaiser, E. T. Acc. Chem. Res. 1989,22, 47–54; Neet, K. E.; Koshland, D. E., Jr. Proc. Natl. Acad. Sci. U.S.A., 1966,56, 1606–1611; Peterson, E. B.; Hilvert, D. Biochemistry 1995, 34, 6616–6620). For example, in one approach cysteine is introduced at a specific position and then reacted with thiosulfonate reagents for the modification of proteins (Kenyon, G. L.; Bruice, T. W. Methods Enzymol. 1977,47,407–430; Wynn, R.; Richards, R. M. Methods Enzymol. 1995, 251, 351–356; Roger L. Lundblad, "Chemical Reagents for Protein Modification", CRC Press, 1991, Chapter 6, pages 59–93). However, the sulfhydryl group of cysteine is a relatively reactive functional group in proteins and may therefore readily and often indiscriminately react with various cysteine modifying agents (e.g., cysteinyl residues are easily alkylated, aceylated and arylated).

Modification of cysteine residues has historically been utilized to improve the selectivity and catalytic activity of proteins, or to inhibit selected enzymes, and particularly cysteine proteinases (see e.g., Curr. Med. Chem. 2002, May 9 (9):979–1002 "Thiol-dependent enzymes and their inhibitors: a review"). However, while various enzymes could be modified using thiol-specific agents, there is to the best of the inventors knowledge no known example of cysteine modification that was reported to inhibit activity of viral enzymes, and especially viral polymerases.

Therefore, although numerous viral polymerase inhibitors are known in the art, all or almost al of them suffer from various disadvantages. Thus, there is still a need to provide compositions and methods to inhibit viral polymerases, and especially the HCV de-novo RNA polymerase.

SUMMARY OF THE INVENTION

The present invention is directed to compositions and methods of inhibition of a viral polymerase, and especially HCV de-novo RNA polymerase, in which contemplated inhibitors comprise two moieties: A first moiety that binds to a an initiation nucleotide binding site of the viral polymerase, and a second moiety that binds to a site proximal to the initiation nucleotide binding site (and especially to a thiol group in the site proximal to the initiation nucleotide binding site). Viewed from another perspective, it should be recognized that contemplated compositions will advantageously improve affinity and retention of a molecule that otherwise would bind only with moderate affinity to the initiation nucleotide binding site as numerous known nucleosides, nucleotides, and their analogs bind only with moderate affinity (e.g., $K_m \sim 10^{-3}M$) to the initiation nucleotide binding site of a polymerase.

In one aspect of the inventive subject matter, a polymerase inhibitor has a structure of F-L-S, wherein F is a first moiety with a heterocyclic base that binds to an initiation nucleotide binding site of a polymerase, and wherein the heterocyclic base forms at least two hydrogen bonds with an RNA template strand that is associated with the polymerase; wherein L is an optional linker in which between one and ten atoms form a contiguous chain, and wherein the contiguous chain covalently connects F with S, and wherein F is covalently bound to S when the linker is not present; and wherein S is a second moiety comprising a compound that binds to a site proximal to the nucleotide binding site of the polymerase, thereby increasing the affinity of the polymerase inhibitor when compared to a polymerase inhibitor having a structure of F-L. Thus, it should be recognized that S acts as a covalent or non-covalent anchor for F.

Particularly preferred inhibitors include a purine heterocyclic base (e.g., guanine), and it is further preferred that the second moiety comprises a thiol-reactive group (e.g., thiol, halogen, or methanethiosulfonate). Alternatively, especially contemplated second moieties may also include a five-membered or six-membered ring that binds to the small pocket proximal to the nucleotide binding site of the polymerase. Particularly preferred polymerases include RNA-dependent RNA polymerases, and especially NS5B of the hepatitis C virus. In another aspect of the inventive subject matter, an exemplary preferred polymerase inhibitor has a structure according to Formula 1

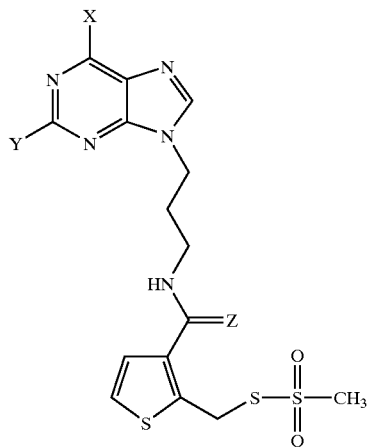

Formula 1 wherein X is OH or $NH_2$, Y is H or $NH_2$, and Z is O or S, and it is even more preferred that in such inhibitors X is O, Y is $NH_2$, and Z is O.

Various objects, features, aspects and advantages of the present invention will become more apparent from the following detailed description of preferred embodiments of the invention, along with the accompanying drawing.

DETAILED DESCRIPTION

The inventors have obtained high-resolution crystal structures of HCV of NS5B at 1.5 Angstrom and a series of small molecule compounds in complex with HCV NS5B near the active site, which enabled the inventors to identify the electron density modification in the HCV NS5B enzyme structure at atomic clarity.

Based on the x-ray crystallographic results, the inventors synthesized various cysteine modifying reagents that bind to the pocket near the active center of the polymerase in a manner such that these reagents will selectively and specifically react with the cysteine residue Cys366 near the active center of the polymerase. Remarkably, the so cysteine-modified polymerases were found to exhibit significantly reduced polymerase activity, and in some cases were even completely inactivated. Consequently, it should be recognized that cysteine modifying reagents may be employed as polymerase inhibitors, and may further be integrated into various antiviral drugs in which the active site of a viral enzyme is proximally located (i.e., within 0.1–15 Angstrom) to a solvent accessible thiol group of a cysteine.

In one particularly contemplated aspect, the inventors observed that the RNA dependent RNA polymerase from hepatitis C virus (NS5B) includes Cys14 near the RNA template binding site, Cys223 near the NTP binding site, and Cys366 near the primer binding site, all or some of which may be modified with a cysteine modifying reagent (a) to reduce the polymerase activity, and/or (b) to provide structural analysis data to identify reactive groups in the enzyme.

For example, in one set of experiments, methyl methanethiosulfonate (MMTS) and the larger, aromatic compound, benzyl methanethiosulfonate (BMTS) were used to probe the reactivity of cysteine residues located in the vicinity of the polymerase active site. Crystals of the viral RNA polymerase were incubated in a stabilizing solution containing between 1 mM and 5 mM concentrations of either MMTS or BMTS for 4 to 8 hours. Subsequent data collection and structure determination using these treated crystals revealed that the compounds successfully modified cysteine residues in the crystallized protein. Our study indicated that MMTS and BMTS selectively (i.e., at least 80%, and more typically at least 90% relative to Cys14 and Cys223) modified Cys366 of HCV NS5B polymerase over all other cysteine residues.

Figure 1:
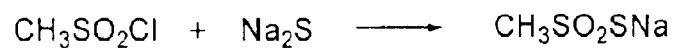
FIG. 1 depicts various structures of exemplary heterocyclic and/or aromatic substituted thiomethylsulfonate derivatives.
Figure 1:
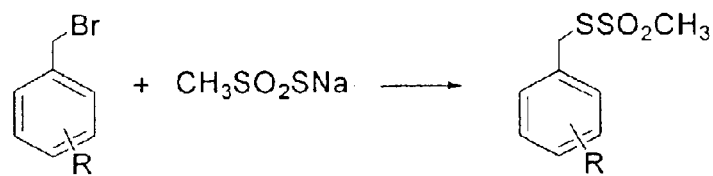
Figure 1:
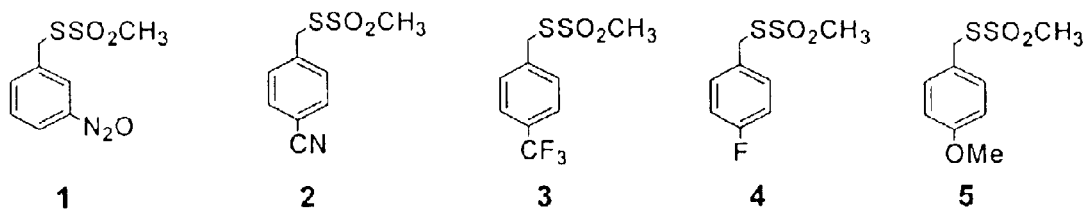
Figure 1:
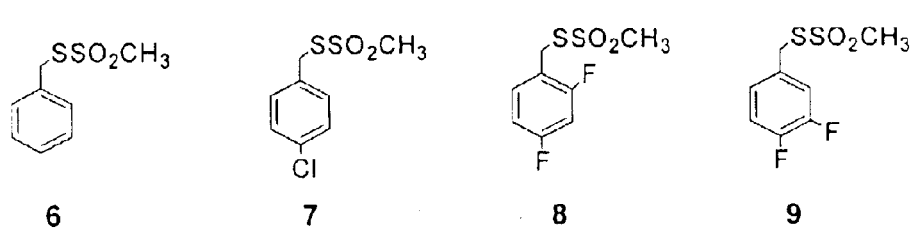
Figure 1:
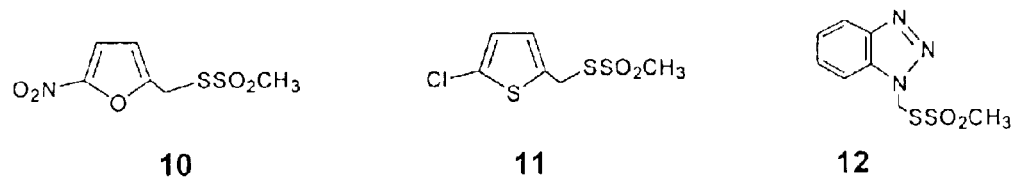
Figure 1:
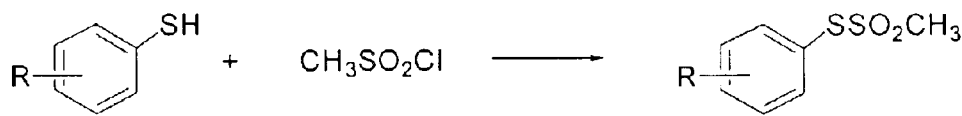
Figure 1:

Cys366 was modified by both compounds (i.e., BMTS and MMTS) and is located in the proximity of the primer-binding site (i.e., initiation nucleotide binding site) of the enzyme. In the case of the larger aromatic compound, BMTS, the phenyl ring was found to pack specifically into a small pocket adjacent to the primer-binding site (hereinafter also referred to as "the pocket" or "the small pocket"). This crystallographic finding was further supported by biochemical assays revealing BMTS as an inhibitor of the NS5B. Based on these observations, it should especially be recognized that specific modification of Cys366 near the primer-binding site may advantageously be employed for rational inhibitor design. Furthermore, it is contemplated that second-generation compounds may even operate without involvement of the Cys366 (i.e., without formation of a covalent bond) by targeting only the small pocket of the NS5B. To explore the binding affinity and specificity to the cysteines near the active sites of NS5B, a exemplary heterocyclic/aromatic-substituted thiomethylsulfonate derivatives were designed and synthesized as depicted in FIG. 1. Binding studies indicated that (5-chlorothiophen-2-yl)methylthiomethylsulfonate shows the highest binding affinity. This compound was also soaked into the polymerase NS5B.

To further explore modified thiomethylsulfonates, guanosine-5'-thiomethylsulfonate and related derivatives were synthesized to explore the binding affinity of these cysteine-modifying agents to the enzyme, and synthesis of exemplary compounds is shown in Scheme 1 below. The synthetic conditions for amino group protection, iodination on the 2'-, 3'-, or 5'-position, deprotection, and thiomethylation followed generally known protocols. Remarkably, all or almost all of the compounds of Scheme 1 showed significant inhibitory activity against HCV NS5B (data not shown).

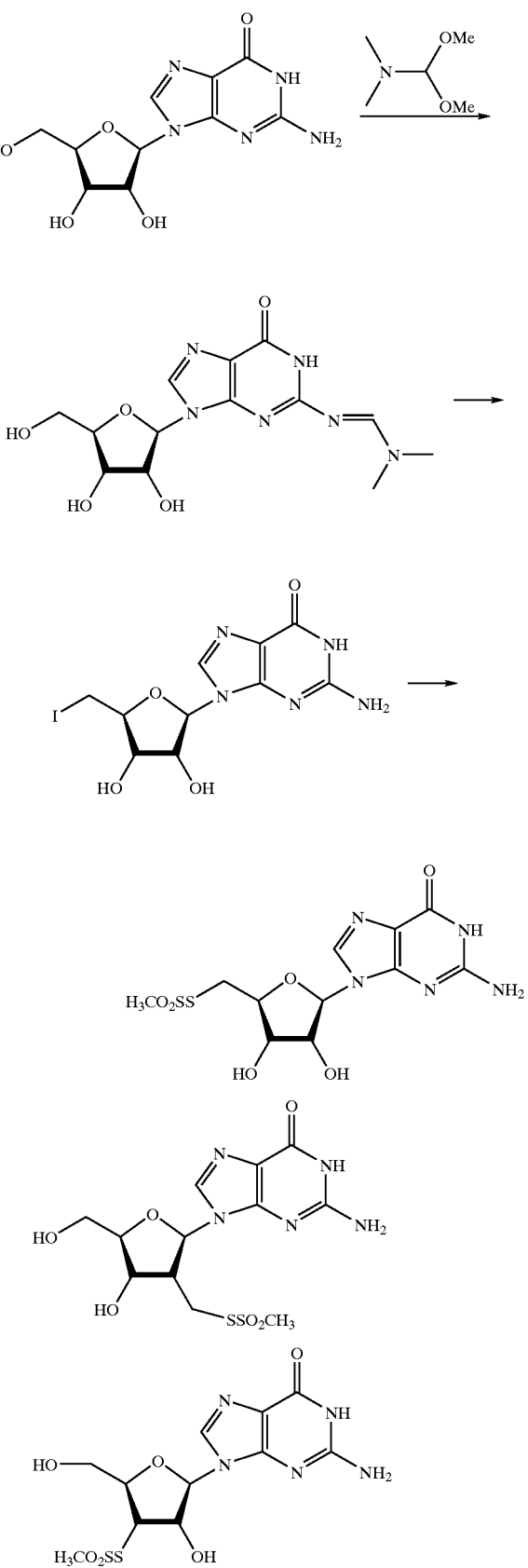

Scheme 1

-continued

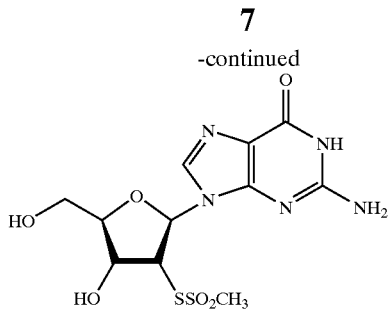

Contemplated Compounds

Based on the inventor's observations (supra), it should be particularly recognized that suitable inhibitors may be rationally designed by combining the binding requirements of the nucleoside tri-phosphate (NTP) or initiation nucleoside (or nucleotide monophosphate or nucleotide diphosphate) with the reactivity of the proximal cysteine residue (Cys366) or the small pocket proximal to the Cys366 in the Hepatitis C virus NS5B polymerase. Cys366 is exposed to the solvent and thus amenable to modification by suitable chemical reagents.

Moreover, depending on the particular nucleoside (analog) employed, and/or where steric optimization of contemplated compounds is desired, it is contemplated that a linker may be included that couples a thiol reactive group (e.g., in MMTS, BMTS, or (5-chlorothiophen-2-yl) methylthiomethylsulfonate) to a moiety that binds to the initiation nucleoside binding site (e.g., a nucleoside, nucleotide, nucleoside analog, or nucleotide analog). As the exact position of the NTP is yet undetermined by X-ray crystallographic techniques, NTP binding (at the initiation nucleoside binding site) was modeled in from the X-ray structure of the bacteriophage Phi6 (Butcher, S. J., Grimes, J. M., Makeyev, E. V., Bamford, D. M. and Stuart, D. I., Science, 410, 235–240 (2001)) by structural alignment techniques well known in the art. The choice of this system was dictated by the fact that it has been shown to be similar to that of the Hepatitis-C virus. The designs for the linkers should thus be able to account for the modeled positioning of the NTP. At present, the position of this moiety is not experimentally determined for the HCV NS5B polymerase. Thus, it is contemplated that the linkers should have a degree of flexibility to incorporate any differences in the position of the modeled NTP compared with the location of the nucleoside tri-phosphates associated with the HCV NS5B.

Therefore, it is generally contemplated that an RNA polymerase inhibitor has a structure as shown below:

First moiety - - - (Optional Linker) - - - Second moiety in which the first moiety binds to an initiation nucleotide binding site, in which the second moiety binds (e.g., covalently via Cys366, or non-covalently in the pocket in which the aromatic portion of BMTS fits) to a site proximal to the initiation nucleotide binding site, and in which an optional linker covalently couples the first to the second moiety. Preferred RNA polymerase are de-novo RNA polymerase, and especially preferred de-novo RNA polymerases are RNA-dependent RNA polymerase from the HCV virus.

In one particularly preferred aspect, it is contemplated that suitable compounds and libraries may be synthesized by solution- and solid-phase combinatorial strategies using MCC or other approaches, wherein each compound in a library has a structure F-(L)-S, wherein F is the first moiety and comprises a heterocyclic moiety/nucleoside/peptidomimetic as a hydrogen bond acceptor and/or donor (which may bind to the initiation nucleoside binding site), wherein (L) is an optional linker, and wherein S is the second moiety that binds to a site proximal to the binding site for F. Preferably, S includes a thiol reactive group (or leaving group). Alternatively, and especially in inhibitors in which S targets the small pocket, it is preferred that S includes a five-membered or six-membered ring. Thus, it is contemplated that some of the preferred compounds react with a cysteine near the active center to form a covalent bond with the enzyme and thereby inhibit the enzymatic activity of HCV NS5B (and other viral enzymes with a reactive thiol proximal to an active site), while other preferred compounds interact non-covalently with a site proximal to the initiation nucleoside (e.g., the small pocket).

With respect to the first moiety it is generally contemplated that the first moiety comprises a naturally occurring nucleoside (preferably guanosine, GMP, GDP, or GTP) or a synthetic nucleoside analog (preferably a guanosine, GMP, GDP, or GTP analog), or the corresponding heterocyclic base thereof. Thus, suitable first moieties may also be characterized by a heterocyclic moiety that forms at least two hydrogen bonds (and more preferably three) with a viral RNA template strand in the RNA polymerase. Exemplary first moieties include those depicted below:

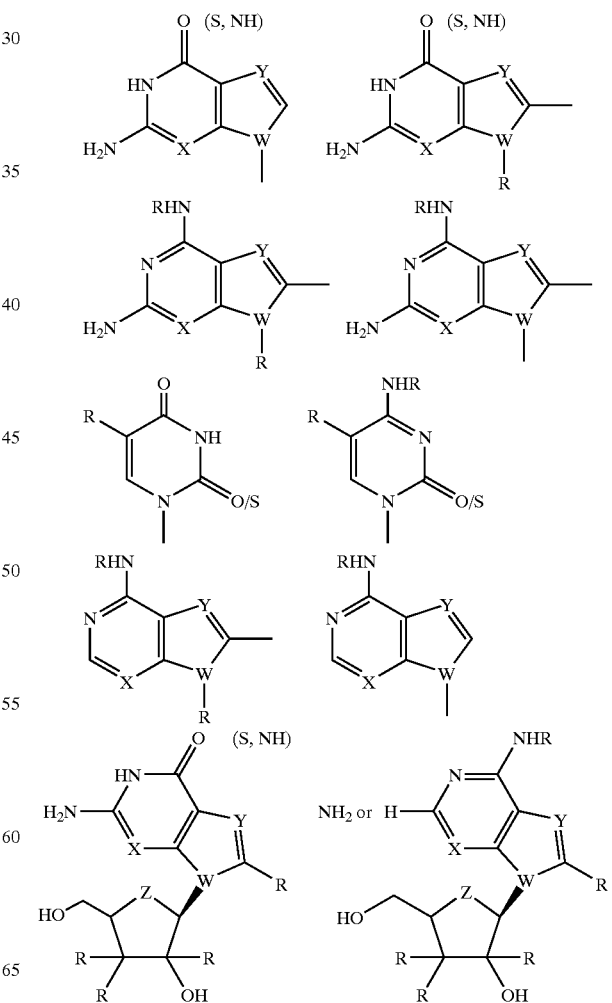

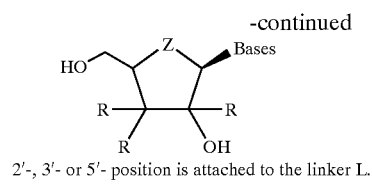

2'-, 3'- or 5'- position is attached to the linker L.

X, W = N, CH, CR, C—L
Y = N, CH, CR, C—L
Z = O, S, NH, NR, CH$_2$, CHR, none
R = H, OH, SH, NH$_2$, N$_3$, NHR, NRR', NHCO, OCO, COOH, COOR, CONH$_2$, alkyl, alkenyl, alkynyl, aryl, heterocycles etc.
Bases = natural and unnatural heterocycles with N, S, and/or O atoms Furthermore, particularly suitable alternative exemplary first moieties may include ribofuranosylimidazole nucleosides, dihydropyrimidine nucleosides, or various substituted N-substituted benzodiazepine nucleosides and synthesis of such nucleoside analogs is described in co-pending international application with the Ser. No. PCT/US02/34025, which is incorporated by reference herein. Further contemplated exemplary first moieties may include 7-deazapurine nucleosides, 9-deaza-C-nucleosides, 7-deaza/8-azaguanosine nucleosides, or 7-deazapurine/toyocamycin nucleosides, and synthesis of such nucleoside analogs is described in co-pending international patent application PCT/US02/40416, which is incorporated by reference herein. Still further contemplated first moieties may include 4,5,6-trisubstituted uridine and/or cytidine nucleoside analogs as described in co-pending international patent application PCT/US02/35558, which is incorporated by reference herein.

Yet further contemplated first moieties may include piperazino-pyrimidine nucleosides or tricyclic nucleosides, the synthesis of which is described in co-pending international patent application PCT/US02/40415 which is incorporated by reference herein. Additionally contemplated first moieties may also include various 2-C-substituted purine nucleosides, 3-deoxy-6-substituted purine nucleosides, substituted 2-thioadenosine nucleosides, 2-amino-6,8-disubstituted purine nucleosides, 2,8-disubstituted guanosine nucleosides, 6-substituted purine nucleosides, various 2,6-disubstituted and 2,6,8-trisubstituted adenine nucleosides, and/or 6,8-disubstituted adenosine nucleosides, the synthesis of which is described in co-pending international patent application PCT/US02/40414, which is incorporated by reference herein.

Still further contemplated first moieties will include pyrazolopyrimidine nucleosides, pyrrolidinopyrimidinone nucleosides, and/or benzimidazole nucleosides, the synthesis of which is described in co-pending international patent application PCT/US02/40365, which is incorporated by reference herein. Of course, it should be recognized that where nucleosides or nucleotides are synthesized, such compounds may be converted to the corresponding heterocyclic bases (aglycon) using various methods well known in the art (e.g., enzymatic or non-enzymatic hydrolysis).

Figure 2:
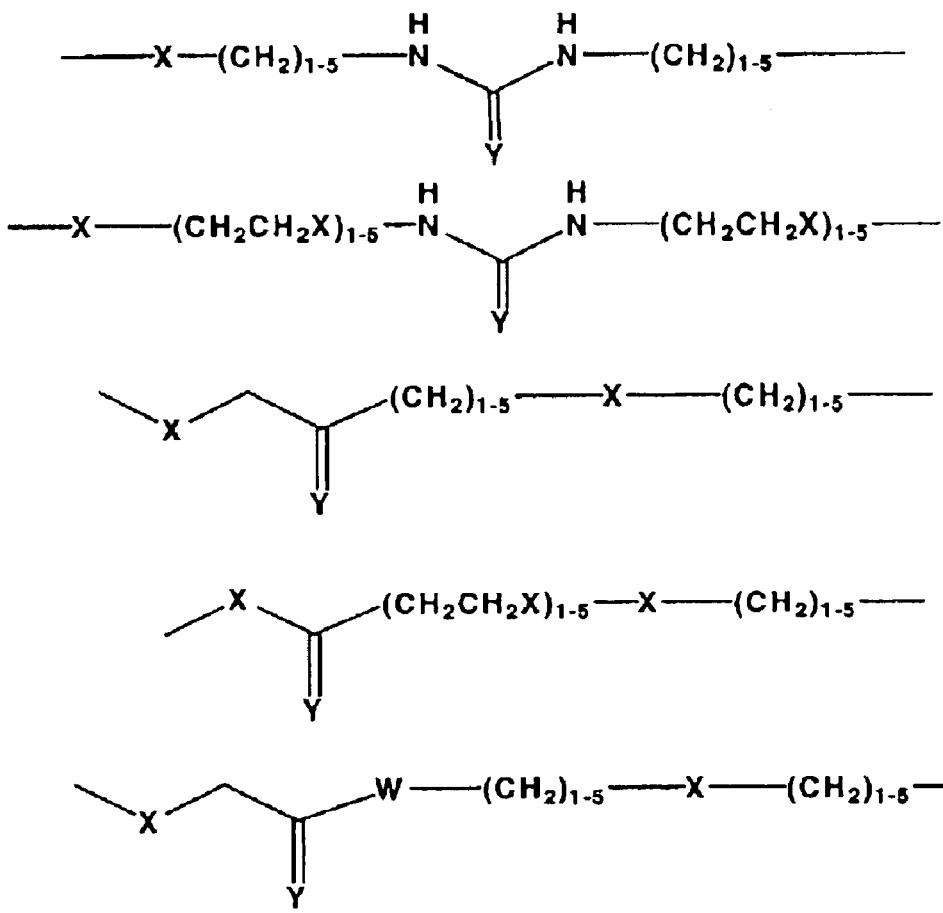
FIG. 2 depicts various structures of exemplary linkers for contemplated compounds.
Figure 3:
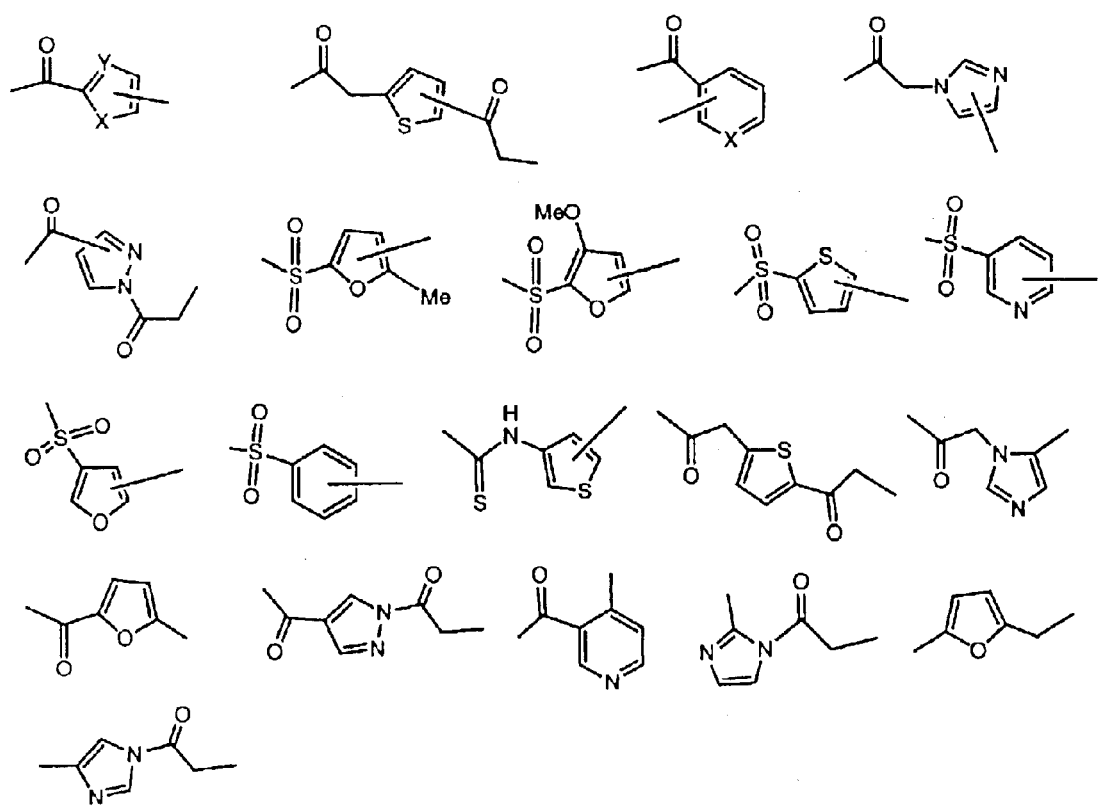
FIG. 3 depicts various structures of exemplary linker extensions for contemplated compounds.

With respect to the linker it is contemplated that depending on the particular spatial properties of the first and/or second moiety, a linker may be omitted altogether. Thus, the linker may also be viewed as a covalent bond between the first moiety and the second moiety. However, where desirable or dictated by the particular spatial properties of the first and/or second moieties, it is generally contemplated that the linker separates the first moiety from the second moiety at a distance between about 1 Angstrom and 50 Angstrom. Therefore, particularly preferred linkers may include a contiguous chain of 1 to about 20 atom, wherein the first moiety is covalently coupled to the chain on one end (or position proximal to the one end), and wherein the second moiety is covalently coupled to the chain on the other end (or position proximal to the other end). Moreover, suitable linkers may themselves include further points of covalent and/or non-covalent interaction with the active site to increase affinity of the inhibitor to the active site. An exemplary collection of suitable linkers is depicted in FIG. 2, and a collection of suitable linker extensions (covalently bound to the linker) is shown in FIG. 3.

Figure 4:
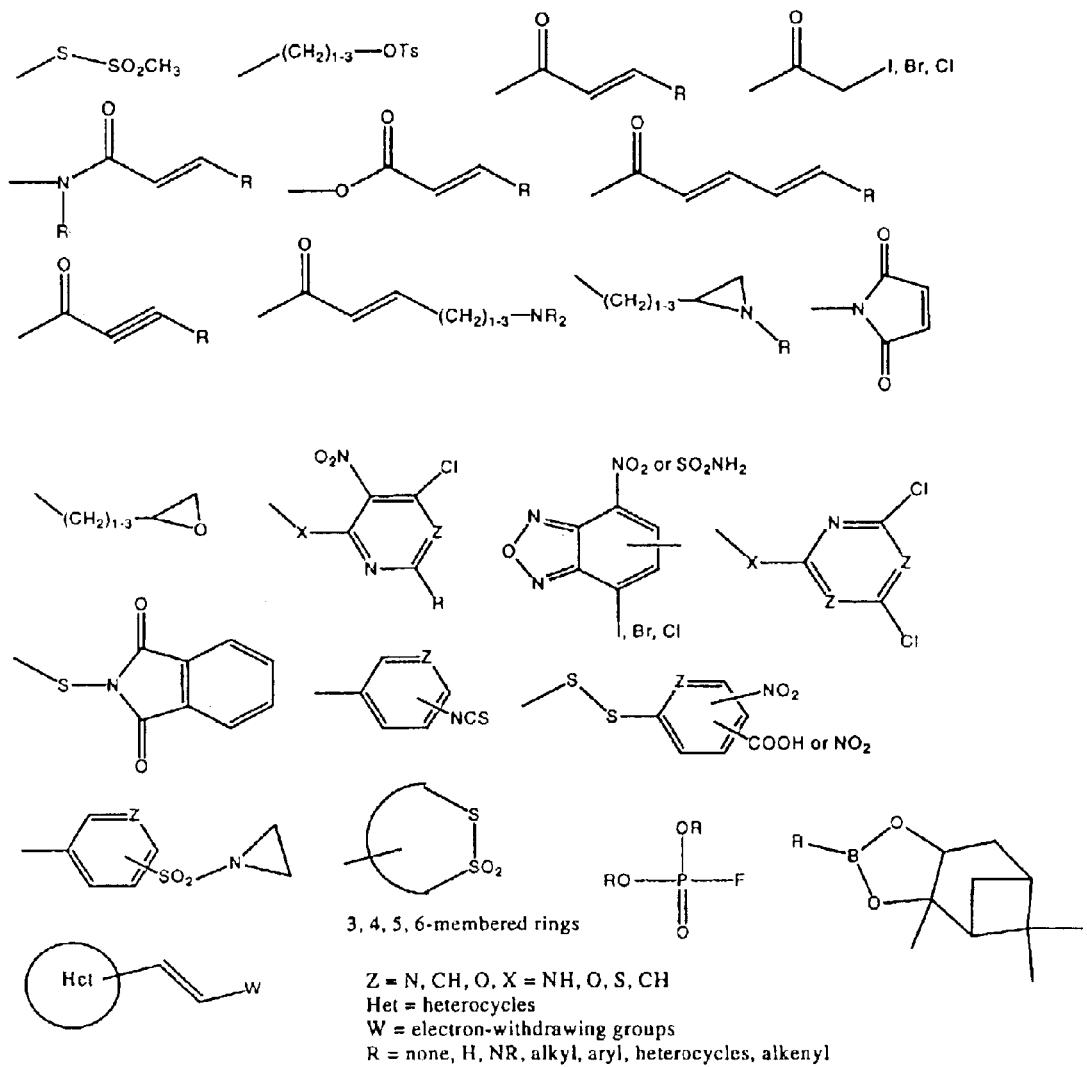
FIG. 4 depicts various structures of exemplary reactive groups and/or leaving groups for contemplated compounds.

Particularly contemplated second moieties comprise a reactive group that reacts with a cysteine thiol of the RNA polymerase, wherein the cysteine thiol is in relatively close spatial relationship to the active site (e.g., Cys366). Consequently, all known disulfides, leaving groups and thiol-reactive groups are considered suitable for use herein. An exemplary collection of suitable reactive groups and leaving groups is shown in FIG. 4.

Therefore, it is contemplated that interaction and/or binding of the second moiety with the site proximal to the initiation nucleoside binding site will result—at least in some cases—in formation of a covalent bond between the inhibitor and the RNA polymerase. However, it is contemplated that alternative second moieties may include a structure that binds to the site proximal to the initiation nucleotide binding site (e.g., the small pocket) via a non-covalent bond, wherein binding may be mediated via a hydrophobic bond, π-stacking interaction, an ionic bond, an electrostatic bond, and/or a hydrogen bond. While the particular nature of such second moieties will typically depend on the exact geometry and physicochemical properties of the site proximal to the initiation nucleotide binding site, it is contemplated that where the small pocket is targeted, suitable second moieties will preferably include a group that has a five-membered ring or a six-membered ring.

Figure 5:
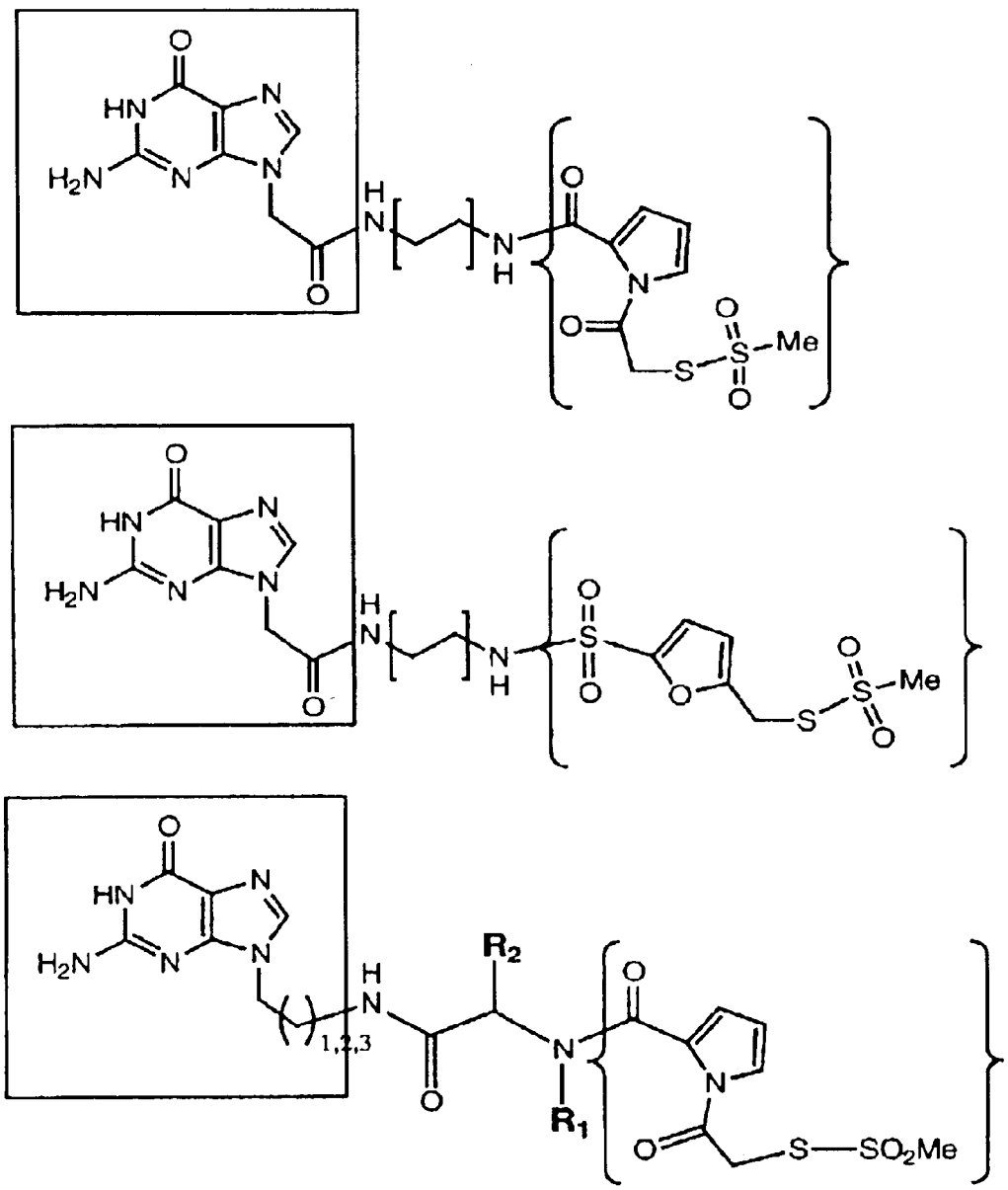
FIGS. 5–10 depict various structures of exemplary polymerase inhibitors according to the inventive subject matter.
Figure 6:
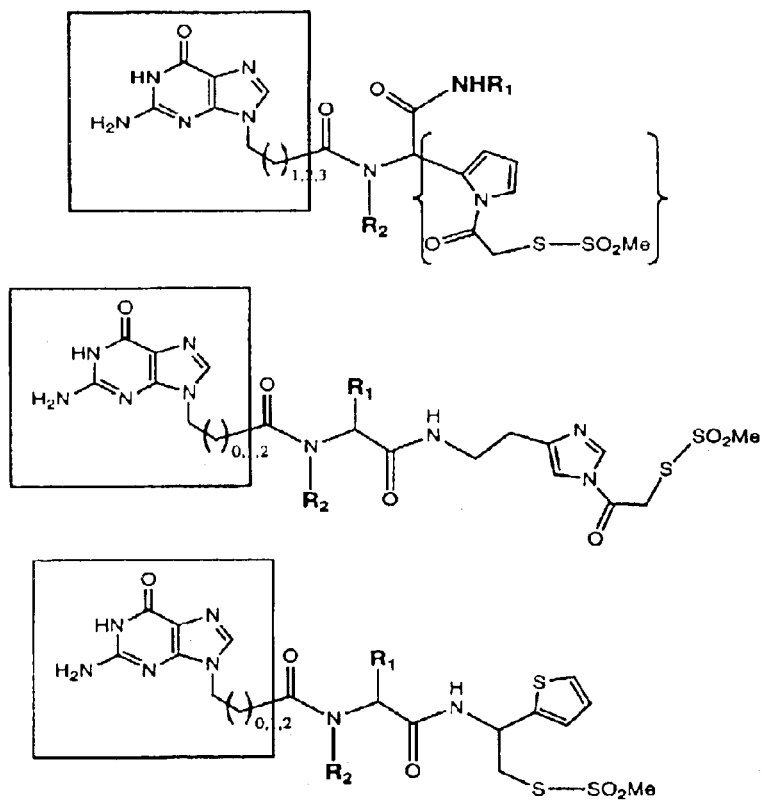
Figure 7:
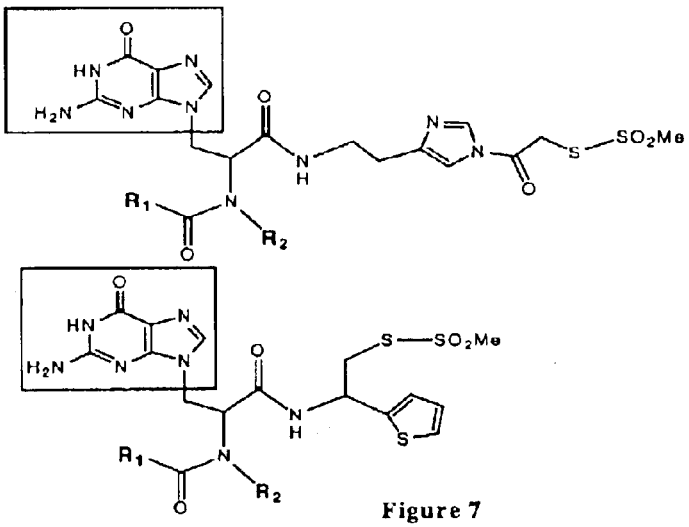
Figure 8:
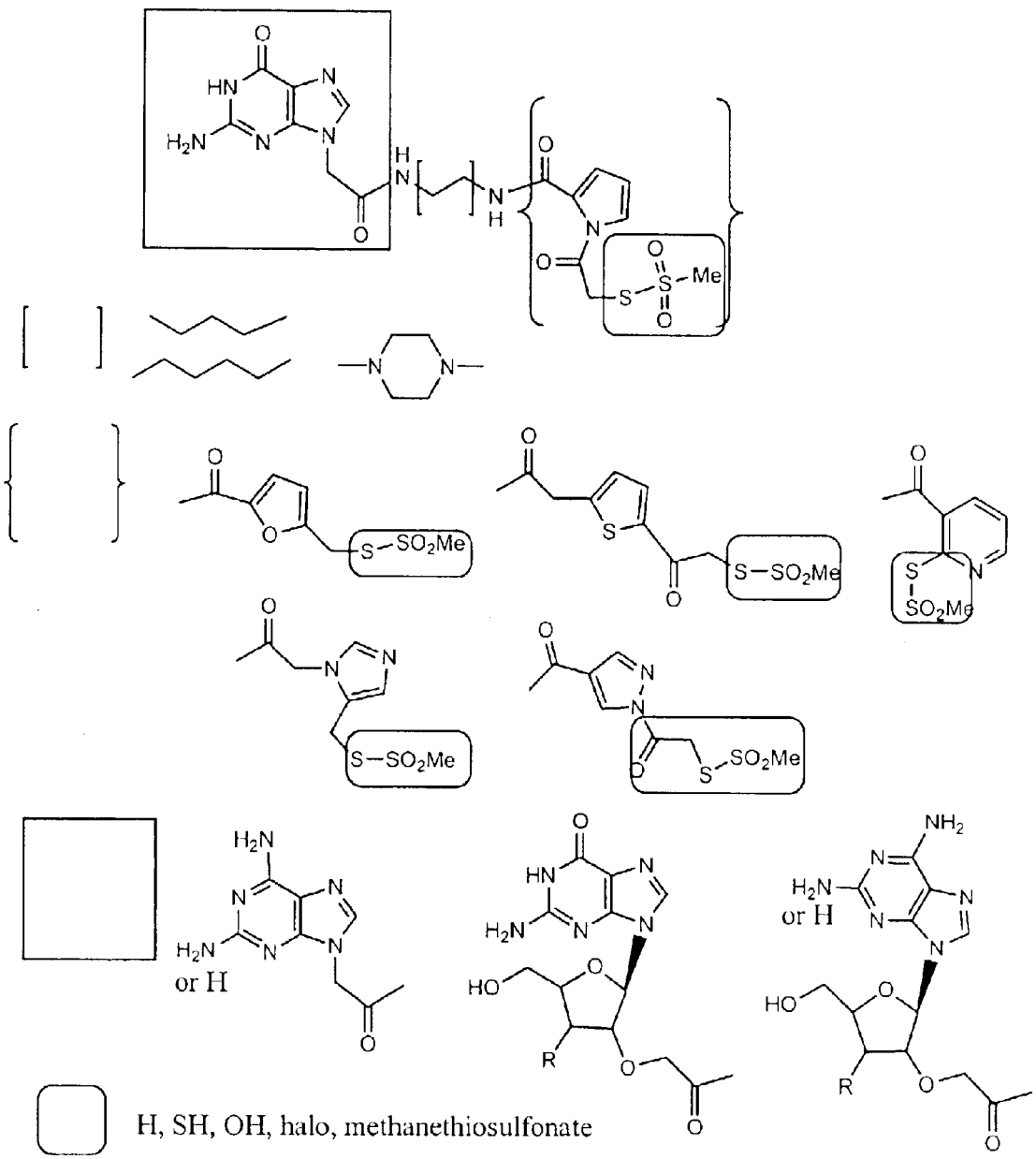
Figure 9:
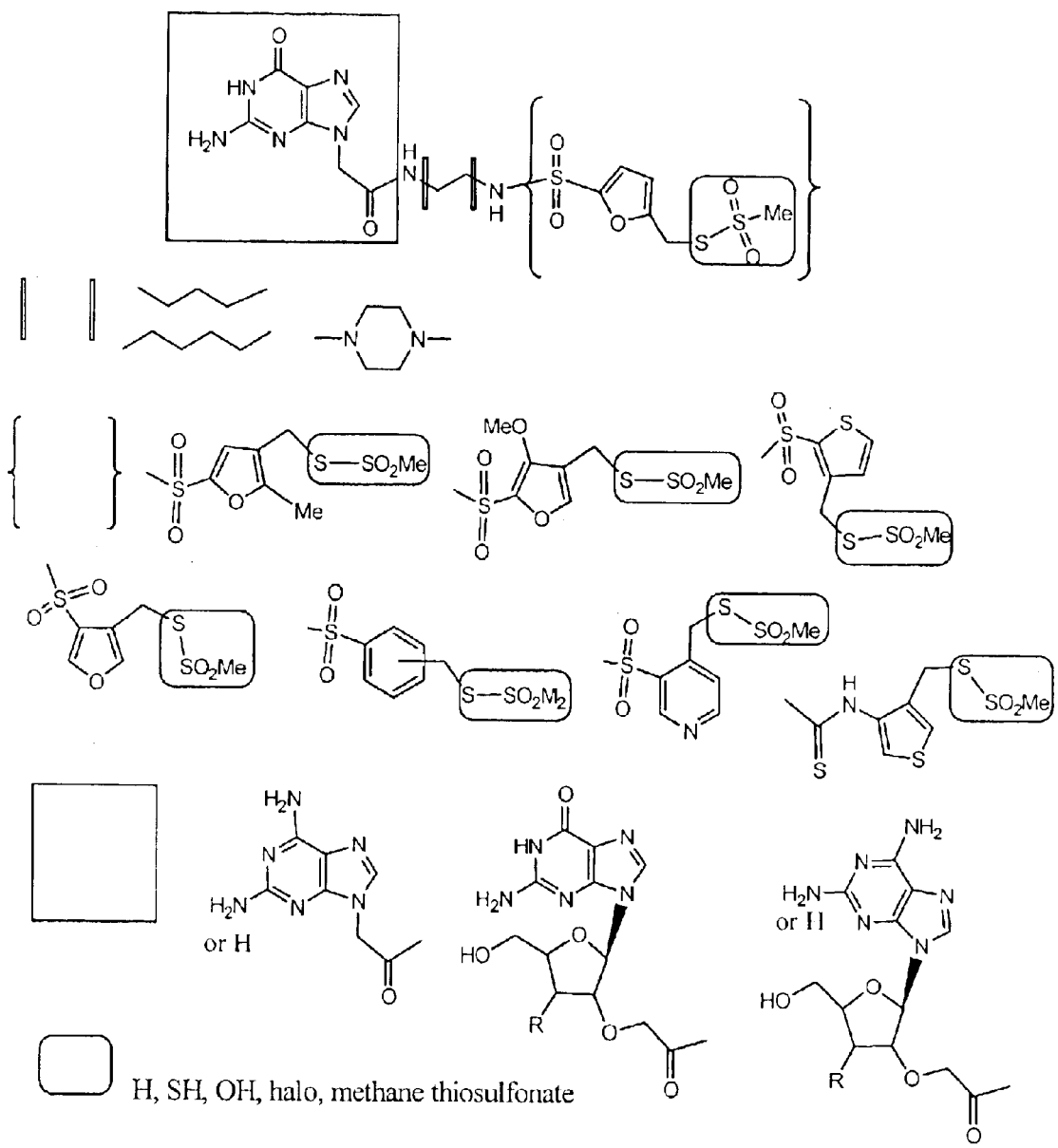
Figure 10:
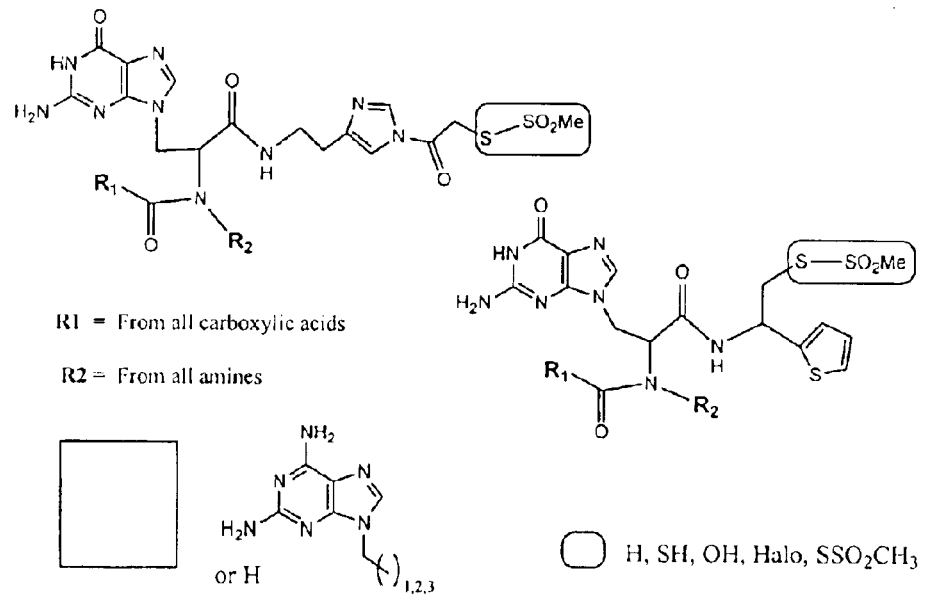

Exemplary contemplated inhibitors are depicted in FIGS. 5–10. For example, where it is preferred that the first moiety is a guanine, the linker comprises a diamine, and the second moiety comprises a thiol reactive group, suitable contemplated compounds may have a structure as shown in FIG. 5, in which the first moiety is drawn in a square, and the second moiety in brackets. In this example, the second moieties in FIG. 5 comprise a thiol-reactive group. Where it is desired that the linker includes one or more side chains, contemplated compounds may have a structure as depicted in FIGS. 6 and 7. Still further contemplated variations of contemplated compounds are shown in FIG. 8, wherein various first moieties are depicted in squares, various linkers in square brackets, and various second moieties in brackets. Further contemplated alternative thiol-reactive groups are shown in round-cornered squares. It should be appreciated that all combinations of first and second moiety, linker, and thiol-reactive group are contemplated. Similarly, additional contemplated compounds are shown in FIG. 9, wherein various first moieties are depicted in squares, various linkers in open bars, and various second moieties in brackets. Further contemplated alternative thiol-reactive groups are shown in round-cornered squares. Again, it should be appreciated that all combinations of first and second moiety, linker, and thiol-reactive group are contemplated. Exemplary linker extensions are depicted in FIG. 10 (alternative thiol-reactive groups are shown in round-cornered squares).

Therefore, it should be recognized that contemplated compounds particularly include polymerase inhibitors of the structure F-L-S, wherein F is a first moiety comprising a heterocyclic base that binds to an initiation nucleotide binding site of a polymerase, and wherein the heterocyclic base forms at least two hydrogen bonds with an RNA template strand that is associated with the polymerase; wherein L is an optional linker in which between one and ten atoms form a contiguous chain, and wherein the contiguous chain covalently connects F with S, and wherein F is covalently bound to S when the linker is not present; and wherein S is a second moiety comprising a compound that binds to a site proximal to the nucleotide binding site of the polymerase, thereby increasing the affinity of the polymerase inhibitor when compared to a polymerase inhibitor having a structure of F-L.

The term "heterocyclic base . . . binds to an initiation nucleotide binding site of a polymerase" as used herein means that the heterocyclic base occupies the initiation nucleotide binding site in a manner that precludes binding of an initiation nucleotide to the initiation nucleotide binding site of a polymerase at the same time the heterocyclic base is bound. Moreover, binding of the heterocyclic base typically has an affinity of no more than $5 \times 10^{-2}$ M, and involves formation of several hydrogen bonds between the heterocyclic base and the template strand and/or the polymerase. As also used herein, the term "RNA template strand . . . is associated with the polymerase" means that the RNA strand is disposed in the polymerase in a manner consistent with initiation of replication (e.g., terminal nucleotide accessible at active site). As still further used herein, the term "a site proximal to the nucleotide binding site" refers to a solvent accessible surface of the polymerase that is no further than 50 Angstrom away from the heterocyclic base bound to the initiation nucleotide binding site. A particularly preferred site is the Cys366, and the small pocket of the polymerase. It should be recognized that binding of the heterocyclic base to the initiation nucleotide binding site as well as binding of the second moiety to the site proximal to the nucleotide binding site of the polymerase may be determined by various methods well known in the art (e.g., limited proteolysis and identification of Cys366 modified fragments, or X-ray diffraction analysis of crystals soaked with second moiety).

Especially preferred polymerase inhibitors of the structure F-L-S will therefore include a first moiety F that comprises a purine (most preferably a guanine), and a second moiety S that comprises a thiol-reactive group (e.g., methanethiosulfonate, a thiol, or a halogen). Alternatively, or additionally, the second moiety may also comprise a five-membered or six-membered ring that binds to a small pocket proximal to the nucleotide binding site of the polymerase. It is also contemplated that the polymerase is a RNA-dependent RNA polymerase, and most preferably NS5B from a hepatitis C virus.

In still further preferred aspects, suitable polymerase inhibitors will have a structure according to Formula 1

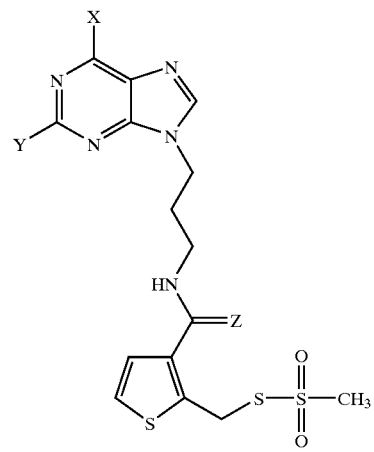

Formula 1 in which X is OH or NH$_2$, Y is H or NH$_2$, and Z is O or S, and most preferably in which X is O, Y is NH$_2$, and Z is O.

Synthesis of Contemplated Compounds

It is generally contemplated that the compounds according to the inventive subject matter may be prepared in numerous manners, and especially preferred manners of synthesis include combinatorial synthesis (e.g., at least one component bound to solid phase), and classic solution based synthesis.

For example, as depicted in Scheme 2 below, guanine is coupled to a solid phase and is reacted with 1-bromo-3-azidopropane to form the corresponding 9-aminoalkylated guanine. The so formed modified guanine is then reacted with an electrophilic reagent (here: activated ester-substituted heterocycle) that includes a sulfonyl-reactive group to form the desired compound.

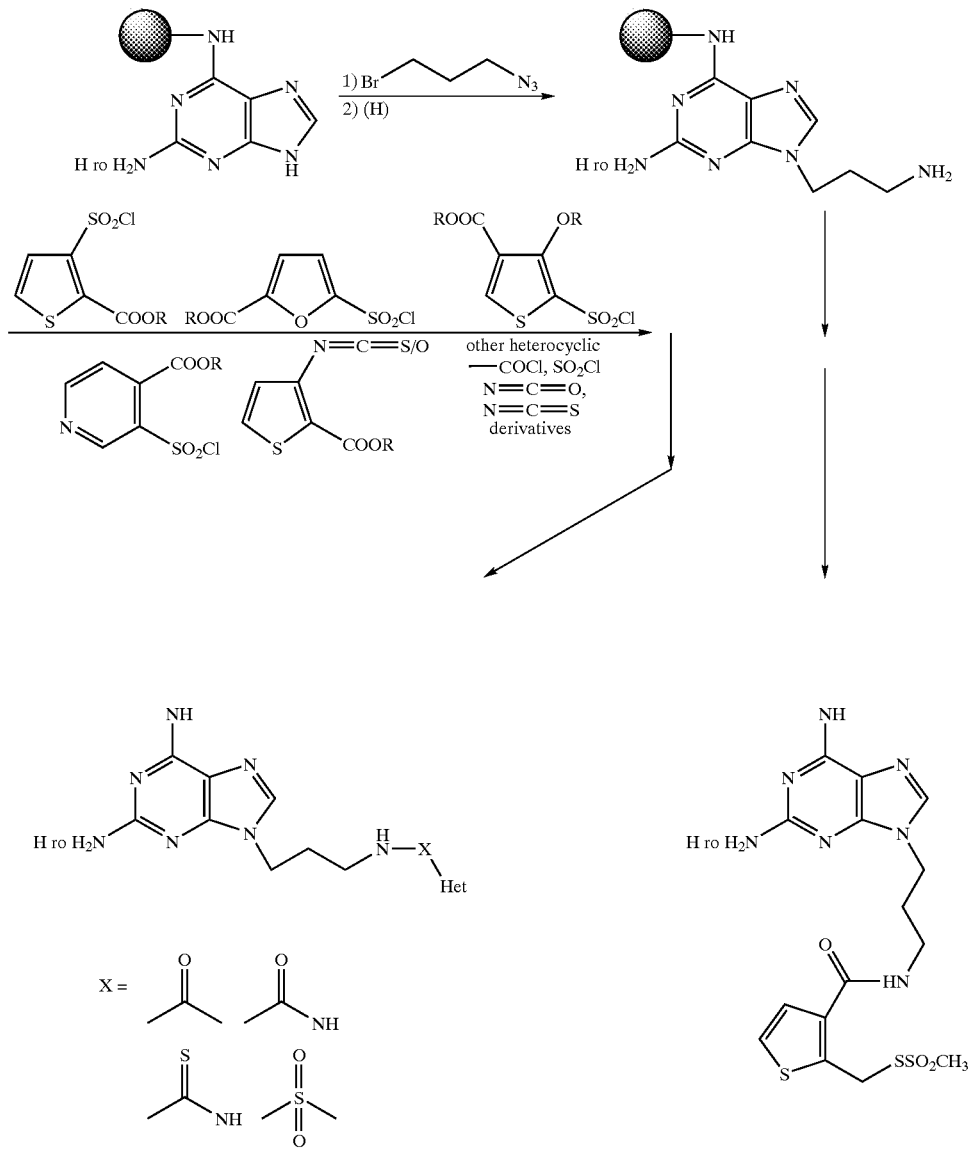

Scheme 2

50

Alternatively, as depicted in Schemes 3 and 4 below, linkers may be modified with one or more substituents (linker extensions) in a reaction between the modified heterocyclic base and the second moiety. Here, extensions are incorporated via a primary amine and an aldehyde, wherein all amines and aldehydes are contemplated suitable for use herein. Among other advantages, it should be recognized that such modified linkers may include additional functional groups that may interact with the polymerase, the template strand, and/or metal ions. Scheme 3 further depicts alternative first moieties in boxes, alternative second moieties in brackets, and alternative thiol-reactive groups in round-cornered rectangles. Of course, it should be appreciated that all combinations of depicted moieties and thiol reactive groups are contemplated.

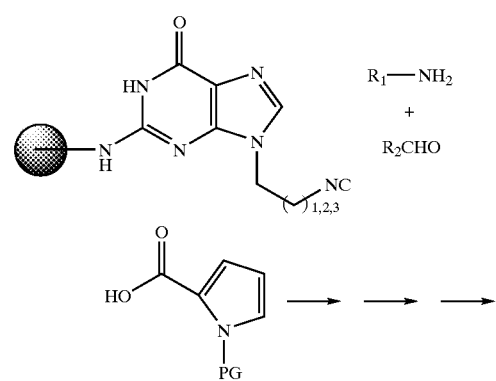

Scheme 3

15
-continued
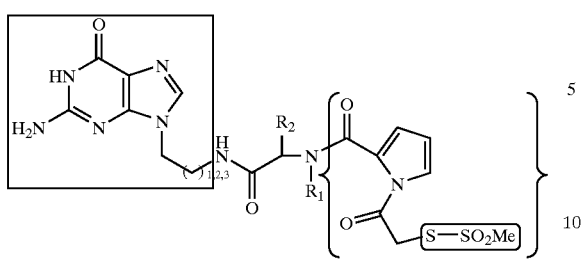
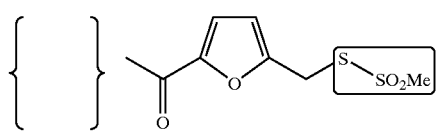
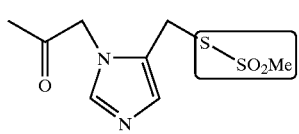
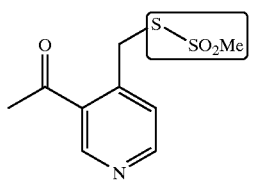
16
-continued
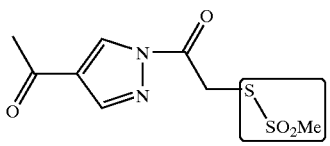
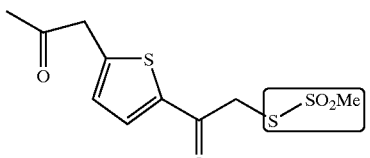
R1 = From all primary amines
R2 = From all aldehydes
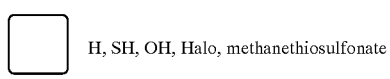 H, SH, OH, Halo, methanethiosulfonate
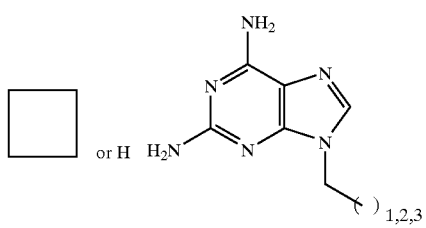
Scheme 4
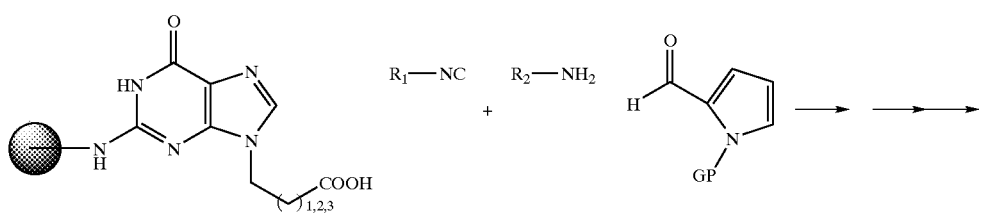
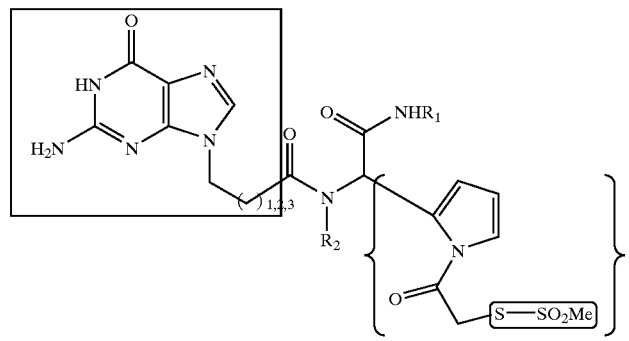
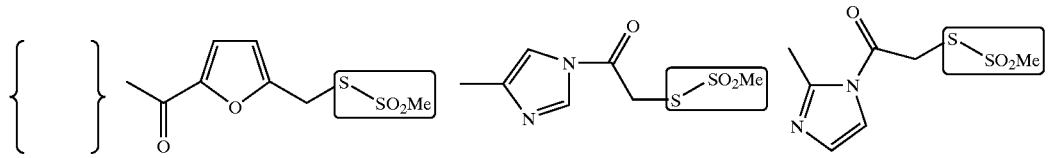

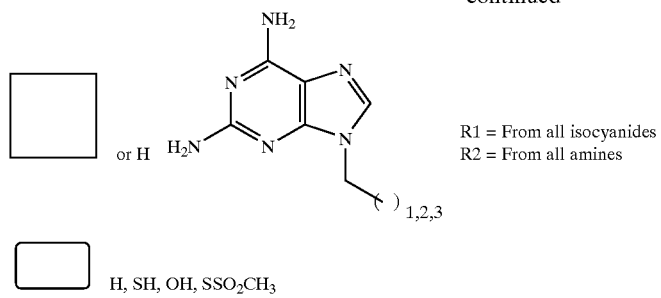

Similarly, where it is desirable that the linker includes functional groups (e.g., hydrogen acceptor groups, or polar groups), suitably substituted first and second moieties may be reacted to form a linker with such desired groups (e.g., to form a peptide-type bond) as depicted in Schemes 5–7 below. Of course it should be recognized that such linkers may still further be modified using reagents as shown in Schemes 3–4 above.

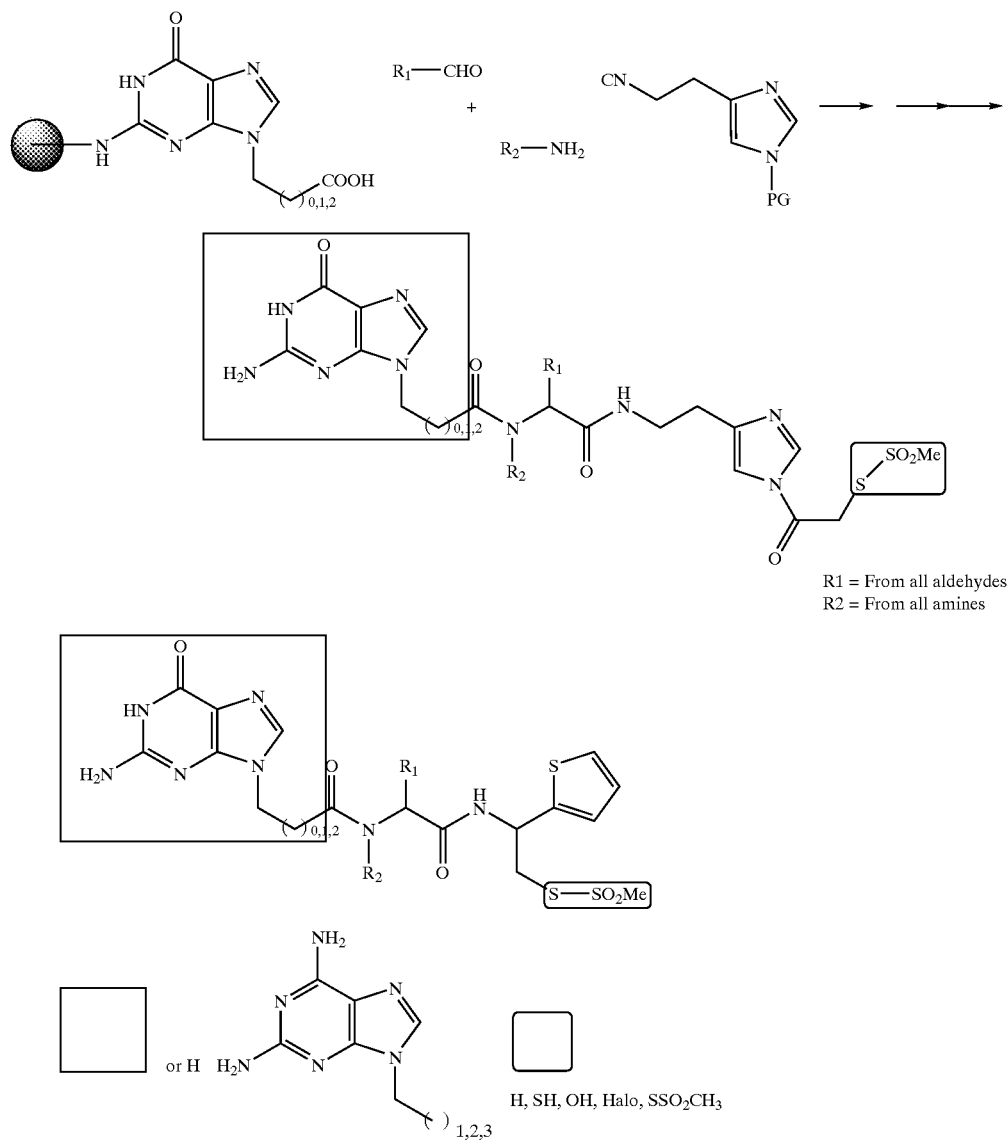

Scheme 6
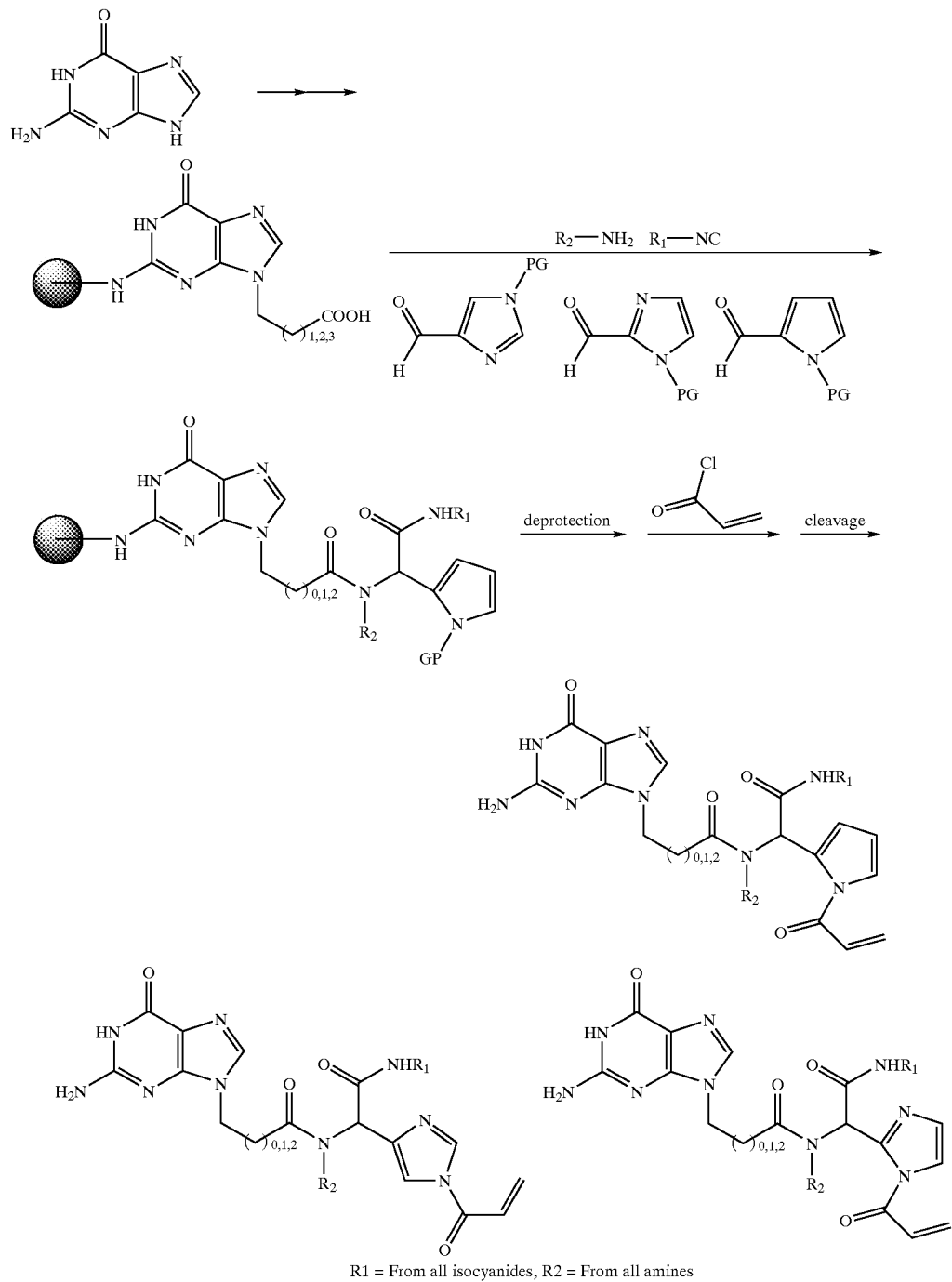
R1 = From all isocyanides, R2 = From all amines
Scheme 7
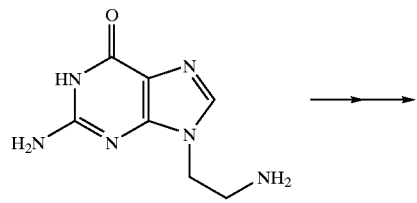

-continued

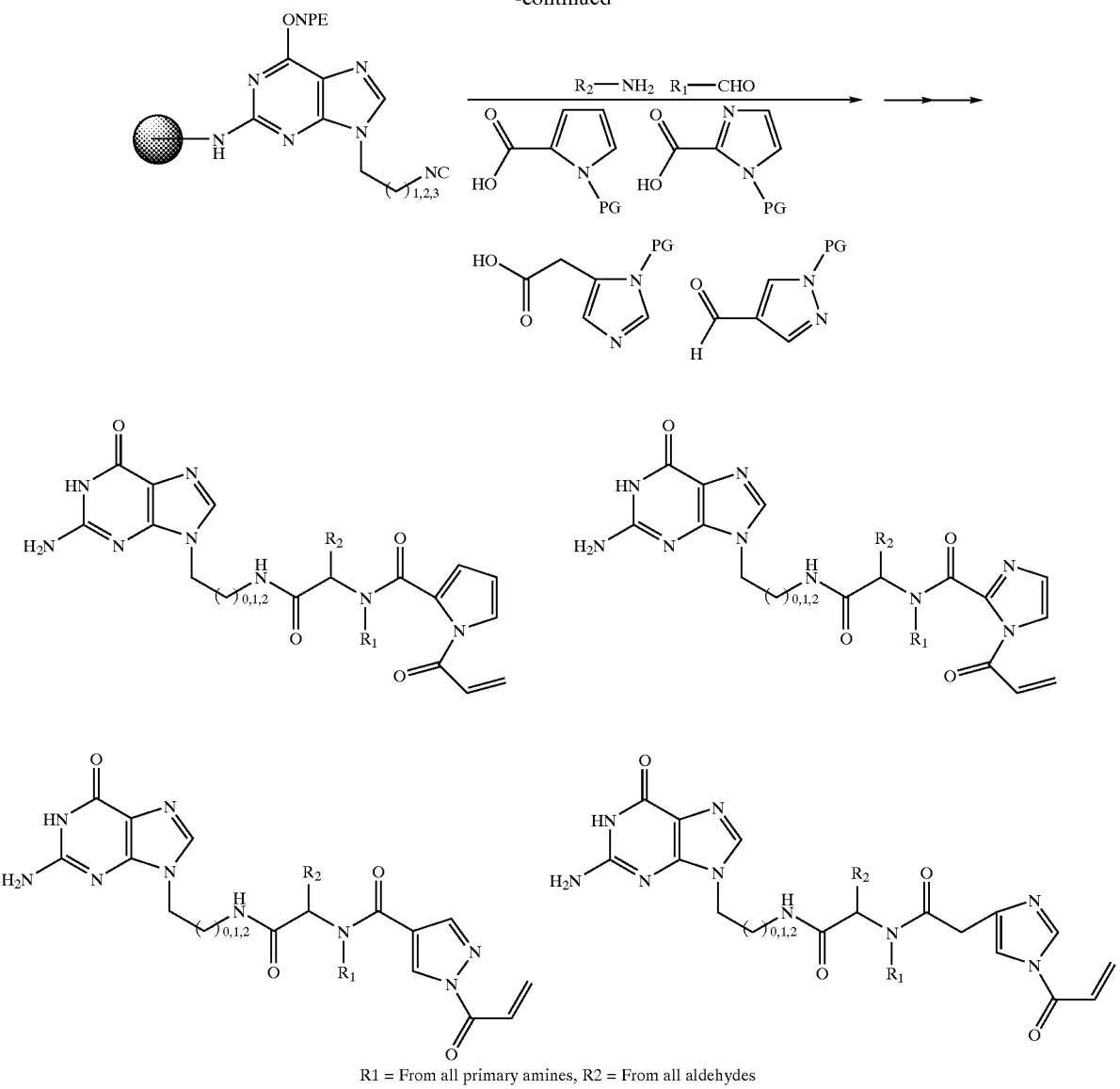

R1 = From all primary amines, R2 = From all aldehydes

Contemplated Uses of Compounds according to the Inventive Subject Matter

The inventors discovered that the compounds according to the inventive subject matter are particularly suitable to inhibit a polymerase, and especially a RNA-dependent RNA polymerase (e.g., NS5B of the HCV virus).

Therefore, a method of producing an RNA polymerase inhibitor may comprise a step in which an active site and a solvent accessible thiol group proximal to the active site in the RNA polymerase is identified. In another step, a thiol-reactive reagent is reacted with the solvent accessible thiol group, and in a further step, inhibition of the RNA polymerase by the thiol-reactive reagent is measured. In particularly contemplated methods, the thiol-reactive reagent has a first portion and a second portion, wherein the first portion reacts with a solvent accessible thiol group and wherein the second portion interacts with one or more amino acid residues on the enzyme. Particularly preferred second portions will have a molecular weight of between about 15 Da and about 200 Da, however, larger second portions are also contemplated.

It should be appreciated that identification of the active site and the solvent accessible thiol may be performed using various techniques well known in the art, and especially contemplated techniques include biochemical assays and X-ray crystallography. With respect to the step of reacting a thiol-reactive reagent with the solvent accessible thiol group, it should be recognized that numerous such reagents are known in the art, and an exemplary reaction is depicted below (Cysteine thiol+BMTS).

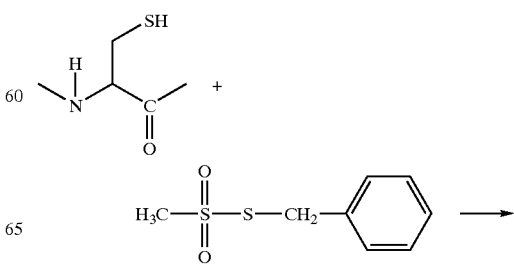

-continued

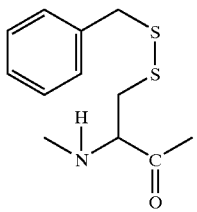

Figure 11:
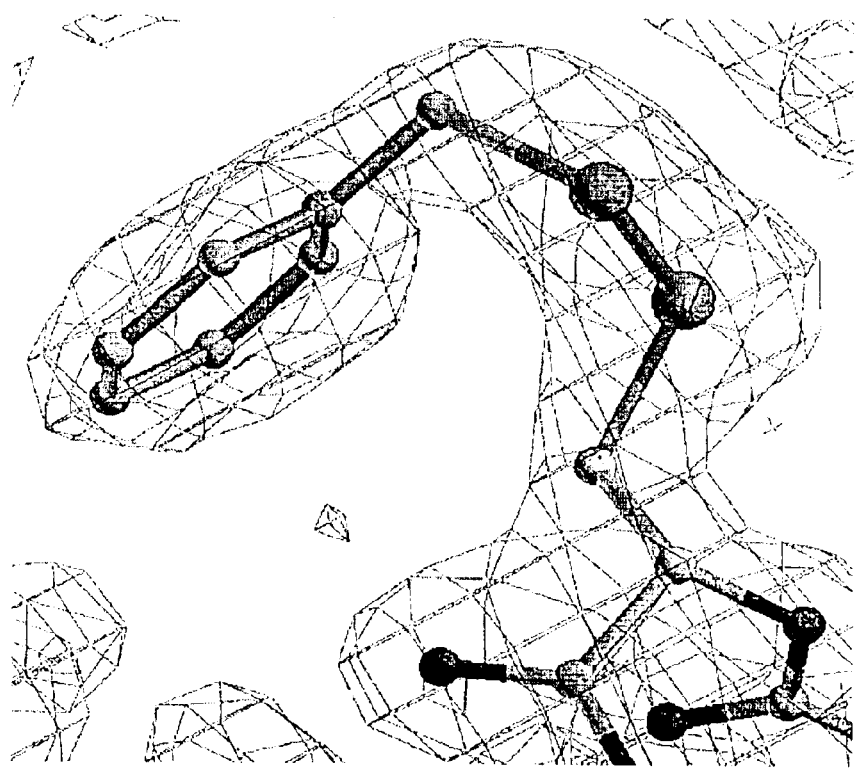
FIG. 11 is an electron density map showing location of the aromatic moiety of BMTS in an HCV RNA-polymerase specific pocket near the primer-binding site, and covalent bond between BMTS and Cys366.
Figure 12:
FIG. 12 is a high-resolution crystal structure of the BMTS-modified NS5B polypeptide of FIG. 11.

In one particular set of experiments, Cys366 of the HCV NS5B polymerase has been reacted with BMTS, and an electron density map clearly reveals that (1) the aromatic moiety of BMTS is located in a HCV specific pocket near the primer-binding site, and (2) that the BMTS formed a covalent bond with the Cys366 thiol group as shown in FIG. 11. The entire NS5B polypeptide with the covalent modification by BMTS in close proximity to the active site is depicted in FIG. 12, in which the BMTS modification and the three aspartate residues of the catalytic site are highlighted.

Figure 13:
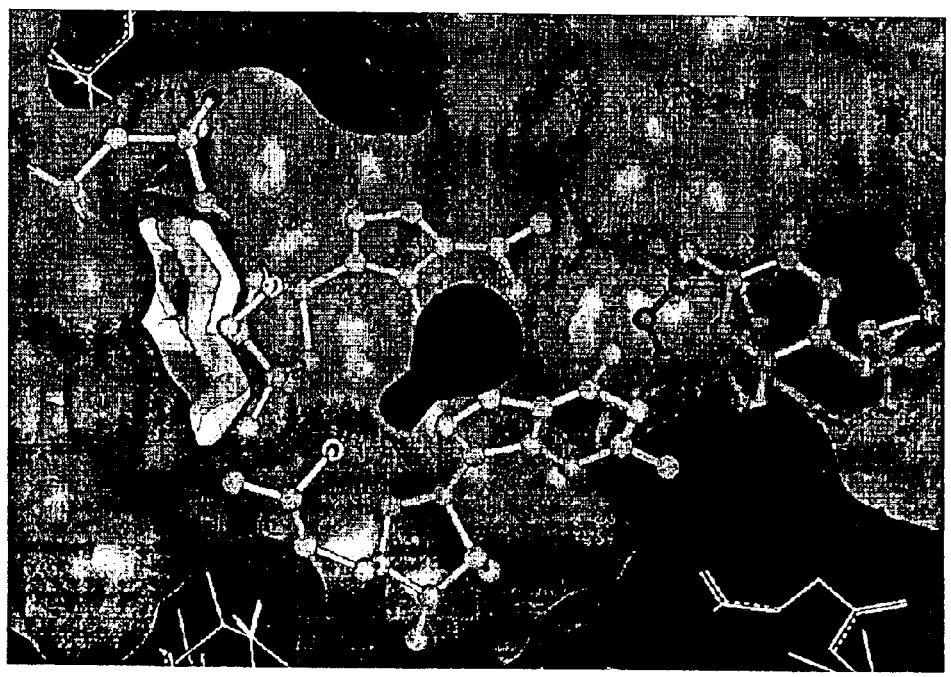
FIG. 13 is a detail view of FIG. 12 showing the active site in which the BMTS modification is shown in bold, in which the template RNA strand is located on the right hand side, and in which the initiation nucleoside and the elongation nucleoside are shown in the center (lower portion and upper portion, respectively).

FIG. 13 depicts a detail view of the active site in which the BMTS modification is shown in white and mint, the template RNA strand on the right hand side is shown in red, and the initiation nucleoside and the elongation nucleoside are shown in amber. As can be clearly seen, the Cys366 thiol group is in close proximity to the initiation nucleoside binding site, and may consequently be employed as an anchor for a substrate or substrate-like molecule to inhibit the NS5B polymerase. Alternatively, the small pocket in which the phenyl moiety of the BMTS is disposed may be employed as a non-covalent anchor site. Thus, as already contemplated above, a bivalent inhibitor may have one portion that binds covalently or non-covalently to a site proximal (i.e., no more than 50 Angstrom) to the initiation nucleoside binding site, and another portion that binds to the initiation nucleoside binding site.

EXAMPLES

Sodium Methanethiosulfonate

Prepared from mesyl chloride and $Na_2S/9H_2O$ based on the reported procedure (Kenyon, G. L.; Bruice, T. W., Methods Enzymol. 1977, 47, 407–430).

Substituted Benzyl Methanethiosulfonate Analogs (FIG. 1, 1–9)

A mixture of substituted benzyl bromide (2 mmol), sodium methanethiosulfonate (2.5 mmol) and anhydrous DMF (5 mL) was stirred at room temperature for 1 hour. The reaction mixture was treated with 5 mL of water, and the mixture was extracted three times with ethyl acetate (15 mL each). The combined ethyl acetate extracts were washed twice with brine, dried over anhydrous sodium sulfate and, concentrated. The residue was purified by flash chromatography on a silica gel column using EtOAc-hexanes (1:3) as an eluent affording a colorless liquids in 65%–95% yields.

Compound 1. $^1$H NMR (CDCl$_3$; 300 MHz): δ8.27 (1H, s), 8.20 (1H, m), 7.73 (1H, m), 7.58 (1H, m), 4.47 (2H, s), 3.09 (3H, s); $^{13}$C NMR (CDCl$_3$; 300 MHz): δ135.4, 130.4, 124.2, 123.5, 51.6, 39.9.

Compound 2. $^1$H NMR (CDCl$_3$; 300 MHz): δ7.65 (2H, d), 7.51 (2H, d), 4.20 (2H, s), 3.05 (3H, s); $^{13}$C NMR (CDCl$_3$; 300 MHz): δ141.1, 133.1, 132.8, 130.1, 118.4, 112.5, 51.6, 40.3.

Compound 3. $^1$H NMR (CDCl$_3$; 300 MHz): δ7.63 (2H, d, J=8.4 Hz), 7.53 (2H, d, J=8.4 Hz), 4.40 (2H, s), 3.00 (3H, s).

Compound 4. $^1$H NMR (CDCl$_3$; 300 MHz): δ7.40 (2H, m), 7.02 (2H, m), 4.40 (2H, s), 3.01 (3H, s); $^{13}$C NMR (CDCl$_3$; 300 MHz): δ131.2, 131.1, 116.4, 116.1, 51.4, 40.2.

Compound 5. $^1$H NMR (CDCl$_3$; 300 MHz): δ7.30 (2H, d), 6.94 (2H, d), 4.37 (2H, s), 3.80 (3H, s), 2.96 (3H, s); $^{13}$C NMR (CDCl$_3$; 300 MHz): δ131.1, 129.1, 127.8, 115.1, 55.6, 51.9, 40.3.

Compound 6. $^1$H NMR (CDCl$_3$; 300 MHz): δ7.40 (5H, m), 4.40 (2H, s), 2.95 (3H, s); $^{13}$C NMR (CDCl$_3$; 300 MHz): δ135.3, 129.4, 129.3, 128.5, 51.3, 40.0.

Compound 7. $^1$H NMR (CDCl$_3$; 300 MHz): δ7.30 (4H, m), 7.51 (2H, d), 4.35 (2H, s), 2.95 (3H, s); $^{13}$C NMR (CDCl$_3$; 300 MHz): δ130.8, 129.4, 130.5, 129.1, 51.4, 40.2.

Compound 8. $^1$H NMR (CDCl$_3$; 300 MHz): δ7.40 (1H, m), 6.95 (2H, m), 4.40 (2H, s), 3.05 (3H, s); $^{13}$C NMR (CDCl$_3$; 300 MHz): δ51.6, 37.3.

Compound 9. $^1$H NMR (CDCl$_3$; 300 MHz): δ7.20 (5H, m), 7.51 (2H, d), 4.35 (2H, s), 3.05 (3H, s); $^{13}$C NMR (CDCl$_3$; 300 MHz): δ125.6, 125.5, 125.5, 118.5, 118.3, 118.2, 117.9, 51.5, 39.9.

Heterocyclic Methanethiosulfonate Analogs (FIG. 1, 10–12)

A mixture of heterocyclic chloromethyl derivative or heterocyclic bromomethyl derivative (2 mmol), sodium methanethiosulfonate (2.5 mmol) and anhydrous DMF (5 mL) was stirred at room temperature for 1 hour. The reaction mixture was treated with 5 mL of water, and the mixture was extracted with ethyl acetate (15 mL, three times). The combined ethyl acetate extracts were washed twice with brine, dried over anhydrous sodium sulfate, and concentrated. The residue was purified by flash chromatography on a silica gel column using EtOAc-hexanes (1:3) as an eluent to afford colorless liquids in 45%–65% yields.

Compound 10. $^1$H NMR (CDCl$_3$; 300 MHz): δ7.30 (1H, d), 6.60 (1H, d), 4.50 (2H, s), 3.40 (3H, s).

Compound 11. $^1$H NMR (CDCl$_3$; 300 MHz): δ6.94 (1H, d, J=0.9 Hz), 6.86 (1H, d, J=0.9 Hz), 4.34 (2H, s), 2.90 (3H, s); $^{13}$C NMR (CDCl$_3$; 300 MHz): δ132.5, 129.9, 127.5, 126.8, 56.0, 39.1.

Compound 12. $^1$H NMR (DMSO-d$_6$; 300 MHz): δ8.09 (1H, d, J=8.7 Hz), 8.01 (2H, d, J=8.4 Hz), 7.63 (1H, m), 7.46 (1H, m), 6.62 (2H, s), 3.43 (3H, s); $^{13}$C NMR (CDCl$_3$; 300 MHz): δ146.1, 132.8, 128.8, 125.4, 120.2, 111.9, 52.4, 51.6.

Heterocyclic Methanethiosulfonate Analogs (FIG. 1, 13–14)

To a solution of heterocyclic thiol derivative (2 mmol) in 5 mL of $CH_2Cl_2$ $CH_3SO_2Cl$ (3 eq.) was added. After stirring at room temperature for 2 hours, the solvent was evaporated, and the residue was purified by flash chromatography on a silica gel column using hexanes-ethyl acetate (4:1) to give the desired products in 35%–55% yields.

Compound 13. $^1$H NMR (CDCl$_3$; 300 MHz): δ7.90 (1H, s), 3.70 (3H, s), 3.60 (3H, s); $^{13}$C NMR (CDCl$_3$; 300 MHz): δ141.3, 129.5, 128.5, 40.7, 32.9.

Compound 14. $^1$H NMR (MDSO-d$_6$; 300 MHz): δ3.70 (3H, s), 2.91 (3H, s), 4.35 (2H, s), 3.05 (3H, s); $^{13}$C NMR (CDCl$_3$; 300 MHz): δ50.1, 16.5.

Thus, specific embodiments and applications of bivalent inhibitors for de-novo RNA polymerases and methods of identifying targets for same have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A polymerase inhibitor according to Formula I

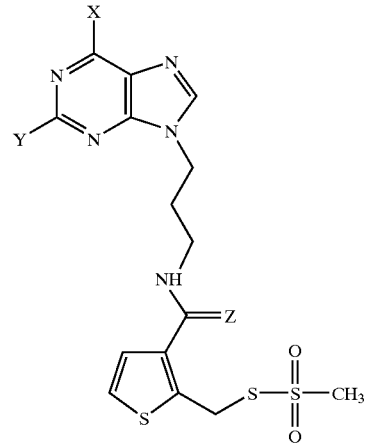

Formula I wherein X is OH or NH$_2$, Y is H or NH$_2$, and Z is O or S.

2. The polymerase inhibitor of claim 1 wherein X is OH, Y is NH$_2$, and Z is O.

* * * * *